(12) United States Patent
Niazi

(10) Patent No.: US 6,462,083 B1
(45) Date of Patent: Oct. 8, 2002

(54) SUPPOSITORY BASE

(76) Inventor: Sarfaraz K. Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 10/010,316

(22) Filed: Nov. 13, 2001

(51) Int. Cl.[7] .......................... A61K 31/20; A61K 47/00
(52) U.S. Cl. .................. 514/560; 514/787; 514/966
(58) Field of Search ................. 514/560, 787, 514/966

(56) References Cited

U.S. PATENT DOCUMENTS

| | | | |
|---|---|---|---|
| 4,837,214 A | 6/1989 | Tanaka et al. | |
| 5,364,879 A * | 11/1994 | Herman | 424/49 |
| 5,405,608 A * | 4/1995 | Xu | 424/520 |
| 6,096,338 A | 8/2000 | Lacy et al. | |
| 6,365,198 B1 * | 4/2002 | Niazi | 424/725 |

* cited by examiner

*Primary Examiner*—William R. A. Jarvis
*Assistant Examiner*—Vickie Kim
(74) *Attorney, Agent, or Firm*—Welsh & Katz, Ltd.

(57) ABSTRACT

This invention provides a suppository base composition of erucic acid and beeswax with improved chemical stability, moldability, and shelf-life. The inventive suppository base also stimulates localized blood flow to the administration site.

7 Claims, No Drawings

SUPPOSITORY BASE

TECHNICAL FIELD

This invention relates to a suppository base comprised of erucic acid and beeswax which provides enhanced chemical stability, moldability, and shelf-life to the suppository product and the medicine contained therein.

BACKGROUND OF THE INVENTION

Suppositories are solid dosage forms of medicine intended for administration via the rectum, vagina, or urethra. Suppositories are useful drug delivery systems in many situations where the patient cannot receive medicine orally, intravenously, or by injection (such as when a patient is vomiting, experiencing seizures, or has an obstruction of the upper gastrointestinal tract); or where only a local effect is needed (such as when a patient has a lower gastrointestinal malady or vaginal infection); or where the medicine is not orally effective and an alternate route of administration is necessary (such as when medicine exhibits first-pass metabolism).

Suppositories are compounded so as to melt, soften, or dissolve in the body cavity (around 98.6° F.) thereby releasing the medication contained therein. Suppository bases should be stable, nonirritating, chemically inert, and physiologically inert. Many commercially available suppositories contain oily or fatty base materials, such as cocoa butter, coconut oil, palm kernel oil, and palm oil, which often melt or deform at room temperature necessitating cool storage or other storage limitations. U.S. Pat. No. 4,837,214 to Tanaka et al. describes a suppository base comprised of 80 to 99 percent by weight of a lauric-type fat having a hydroxyl value of 20 or smaller and containing glycerides of fatty acids having 8 to 18 carbon atoms combined with 1 to 20 percent by weight diglycerides of fatty acids (which erucic acid is an example of). The shelf life of these type of suppositories is limited due to degradation. Other suppository bases contain alcohols, surfactants, and the like which raise the melting temperature but also can lead to poor absorption of the medicine and side effects due to irritation of the local mucous membranes (see for example, U.S. Pat. No. 6,099,853 to Hartelendy et al., U.S. Pat. No. 4,999,342 to Ahmad et al., and U.S. Pat. No. 4,765,978 to Abidi et al.).

The present invention provides one solution to the limitations of the currently available suppository bases as is discussed in the disclosure that follows. Here a suppository base comprised of erucic acid and beeswax provides enhanced chemical stability, moldability, and shelf-life. The composition described in this invention is further expected to enhance the delivery of medicine by increasing localized blood flow thus improving the absorption of medicine contained therein.

SUMMARY OF THE INVENTION

The present invention is directed to a suppository base comprised of erucic acid. Another embodiment of the suppository base is comprised of erucic acid and beeswax. The amount of erucic acid in the composition can range from about 90 to about 99 percent by weight and the amount of beeswax present in the composition can range from about 1 to about 10 percent by weight. The most preferred base composition contains about 10 percent by weight beeswax and about 90 percent by weight erucic acid. Additives such as colorants, preservatives, stabilizers, solvents, and fragrances are also contemplated.

DETAILED DESCRIPTION OF THE INVENTION

Erucic acid or (Z)-13-Docosenoic acid ($\Delta^{13}$cis-decosenoic acid; $C_{22}H_{42}O_2$) is a monoethenoid acid found in the seed fats of Cruciferae and Tropaeolaccae family of plants. It constitutes about 50 percent of the total fatty acids in rapeseed, mustard, and wallflower seeds and about 80 percent of the total fatty acids in nasturtium seeds (K. S. Markley, Fatty Acids Part I, Interscience, New York, Second Ed., 1960)

Erucic acid is prepared by the alkaline hydrolysis of rapeseed oil and further refined by fractional precipitation, crystallization, or acid soap crystallization. Erucic acid can be found in cooking oils, mustards, industrial lubricants, plastic materials, hair care products, and fabric softeners. Erucic acid is thought to be a vasodilator and has been shown to enhance blood flow to the site of administration by laser Doppler imaging.

Preferably, the present inventive suppository base composition is comprised of erucic acid to which beeswax can be added. More preferably, the present invention contains about 90 to about 99 percent by weight erucic acid and beeswax in an amount of about 1 to about 10 percent by weight. Most preferably, the suppository base comprises about 10 percent by weight beeswax and about 90 percent by weight erucic acid. Another embodiment further comprises a colorant, a preservative, a stabilizer, a solvent, a fragrance, or mixtures thereof.

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

EXAMPLES

General Procedure

A general procedure for the formulation of the suppository base is as follows: about 10 percent by weight beeswax is added to about 90 percent by weight erucic acid and the mixture is heated to about 75° C. and stirred until homogenous. The mixture is then poured into molds and allowed to cool. The suppository is then removed from the mold and is ready for use.

Example 1

A suppository containing erucic acid and beeswax was prepared as follows: about 90 g of erucic acid is added to about 9.9 g of beeswax and the mixture is heated gently at 75° C. and stirred until homogeneous. The medicine of interest can be added to the mixture at this stage or when slightly cooler, depending on the heat stability of the particular medicine to be added. Alternatively, the medicine can be dissolved in a solvent such as ethanol prior to adding to the erucic acid-beeswax mixture. The mixture is then poured into molds and allowed to cool naturally or by flash cooling if desired. The suppository is then removed from the mold and is ready for use.

Example 2

A rectal suppository comprising erucic acid, beeswax, and the medicines betamethasole and cinchocaine was prepared as follows: About 0.042 kg of betamethasole valerate and about 0.040 kg of cinchocaine hydrochloride was added to a homogenous melt containing about 64.73 kg of erucic acid and about 7.19 kg of beeswax at a temperature of about 75° C. The medicine and suppository base were mixed gently until homogenous then poured into a mold. Upon cooling the suppository was removed from the mold.

Example 3

A rectal suppository comprising erucic acid, beeswax, and the medicine metoclopramide was prepared as follows: A solution of about 0.630 kg of metoclopramide in 3.70 kg of ethanol was added to a homogenous melt containing about 72.33 kg of erucic acid and about 8.04 kg of beeswax at a temperature of about 75° C. The medicine and suppository base was mixed gently until homogenous and the ethanol evaporated, then poured into a mold. Upon cooling the suppository was removed from the mold.

Example 4

A vaginal suppository comprising erucic acid, beeswax, and the medicine miconazole was prepared as follows: About 12.30 kg of micronized miconazole nitrate was added to a homogenous melt containing about 62.10 kg of erucic acid and about 6.90 kg of beeswax at a temperature of about 75° C. The medicine and suppository base was mixed gently until homogenous then poured into a mold. Upon cooling the suppository was removed from the mold.

Example 5

A rectal suppository comprising erucic acid, beeswax, and the medicine diclofenac was prepared as follows: About 8.08 kg of micronized sodium diclofenac was added to a homogenous melt containing about 122.34 kg of erucic acid and about 13.57 kg of beeswax at a temperature of about 75° C. The medicine and suppository base was mixed gently until homogenous and the ethanol evaporated then poured into a mold. Upon cooling the suppository was removed from the mold.

Example 6

A rectal suppository comprising erucic acid, beeswax, and the medicine acetaminophen was prepared as follows: About 20.2 kg of acetaminophen was added to a homogenous melt containing about 50.0 kg of erucic acid and about 5.8 kg of beeswax at a temperature of about 75° C. The medicine and suppository base was mixed gently until homogenous and the ethanol evaporated then poured into a mold. Upon cooling the suppository was removed from the mold.

Example 7

A rectal suppository comprising erucic acid, beeswax, and the medicine bisacodyl was prepared as follows: About 0.306 kg of micronized biscodyl was added to a homogenous melt containing about 48.33 kg of erucic acid and about 5.37 kg of beeswax at a temperature of about 75° C. The medicine and suppository base was mixed gently until homogenous and the ethanol evaporated then poured into a mold. Upon cooling the suppository was removed from the mold.

Example 8

A rectal suppository comprising erucic acid, beeswax, and the medicines lidocaine and tribenoside was prepared as follows: About 3.28 kg of lidocaine base and about 32.00 kg of tribenoside were added to a homogenous melt containing about 101.52 kg of erucic acid and about 11.27 kg of beeswax at a temperature of about 75° C. The medicine and suppository base was mixed gently until homogenous and the ethanol evaporated then poured into a mold. Upon cooling the suppository was removed from the mold.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims, modifications as fall within the scope of the claims.

I claim:

1. A suppository base composition comprising erucic acid present in an amount of about 90 to about 99 percent by weight and beeswax present in in an amount of about 1 to about 10 percent by weight.

2. The composition of claim 1 further comprising a colorant.

3. The composition of claim 1 further comprising a preservative.

4. The composition of claim 1 further comprising a stabilizer.

5. The composition of claim 1 further comprising a solvent.

6. The composition of claim 1 further comprising a fragrance.

7. A suppository base comprising about 10 percent by weight beeswax and about 90 percent by weight erucic acid.

* * * * *